US011786355B2

(12) United States Patent
McNern et al.

(10) Patent No.: US 11,786,355 B2
(45) Date of Patent: Oct. 17, 2023

(54) RADIAL ADJUSTING SELF-EXPANDING STENT WITH ANTI-MIGRATION FEATURES

(71) Applicant: BOSTON SCIENTIFIC SCIMED, INC., Maple Grove, MN (US)

(72) Inventors: Louis McNern, Donegal (IE); Gary Gilmartin, Foxford (IE); Michael Walsh, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 248 days.

(21) Appl. No.: 17/127,294

(22) Filed: Dec. 18, 2020

(65) Prior Publication Data

US 2021/0236259 A1 Aug. 5, 2021

Related U.S. Application Data

(60) Provisional application No. 62/967,755, filed on Jan. 30, 2020.

(51) Int. Cl.
*A61F 2/04* (2013.01)
*A61F 2/90* (2013.01)
*A61F 2/82* (2013.01)

(52) U.S. Cl.
CPC .................. *A61F 2/04* (2013.01); *A61F 2/82* (2013.01); *A61F 2/90* (2013.01); *A61F 2002/044* (2013.01); *A61F 2230/0091* (2013.01)

(58) Field of Classification Search
CPC ...... A61F 2/04; A61F 2/82; A61F 2/90; A61F 2/8483; A61F 2/07; A61F 2002/044;
(Continued)

(56) References Cited

U.S. PATENT DOCUMENTS 5,064,435 A 11/1991 Porter
5,103,817 A 4/1992 Reisdorf et al.
(Continued)

FOREIGN PATENT DOCUMENTS

EP 2085050 A1 8/2009
EP 2386275 A1 11/2011
(Continued)

OTHER PUBLICATIONS

International Search Report, International Application No. PCT/US2017/060725, dated Feb. 6, 2018.
(Continued)

*Primary Examiner* — Dinah Baria
(74) *Attorney, Agent, or Firm* — Seager, Tufte & Wickhem, LLP (57) ABSTRACT

An esophageal stent may include an expandable framework having a first end, a second end, and a central longitudinal axis extending from the first end to the second end, the expandable framework being configured to expand from a radially collapsed configuration to a radially expanded configuration, and a polymeric outer sleeve disposed radially outward of and spaced apart from a body region of the expandable framework. The expandable framework may include a plurality of anti-migration supports extending radially outward from the body region of the expandable framework toward the polymeric outer sleeve.

19 Claims, 8 Drawing Sheets

(58) Field of Classification Search
CPC .......... A61F 2002/072; A61F 2002/075; A61F 2230/0091
See application file for complete search history.

(56) References Cited

U.S. PATENT DOCUMENTS

| | | | |
|---|---|---|---|
| 5,397,355 A | 3/1995 | Marin et al. |
| 5,425,739 A | 6/1995 | Jessen |
| 5,522,881 A | 6/1996 | Lentz |
| 5,645,559 A | 7/1997 | Hachtman et al. |
| 5,669,930 A | 9/1997 | Igarashi |
| 5,876,448 A | 3/1999 | Thompson et al. |
| 5,937,861 A | 8/1999 | Augustine |
| 6,007,575 A | 12/1999 | Samuels |
| 6,187,034 B1 | 2/2001 | Frantzen |
| 6,395,019 B2 | 5/2002 | Chobotov |
| 6,695,878 B2 | 2/2004 | McGuckin et al. |
| 6,729,356 B1 | 5/2004 | Baker et al. |
| 6,926,724 B1 | 8/2005 | Chu |
| 7,108,715 B2 | 9/2006 | Lawrence-Brown et al. |
| 7,125,464 B2 | 10/2006 | Chobotov et al. |
| 7,150,758 B2 | 12/2006 | Kari et al. |
| 7,235,099 B1 | 6/2007 | Duncavage et al. |
| 7,594,928 B2 | 9/2009 | Headley, Jr. et al. |
| 7,628,804 B2 | 12/2009 | Flagle et al. |
| 7,740,791 B2 | 6/2010 | Kleine et al. |
| 7,806,857 B2 | 10/2010 | Khosravi et al. |
| 7,942,923 B2 | 5/2011 | Gregorich |
| 8,226,708 B1 | 7/2012 | Murch |
| 8,465,538 B2 | 6/2013 | DiMatteo et al. |
| 8,512,414 B2 | 8/2013 | Musani |
| 8,591,570 B2 | 11/2013 | Revuelta et al. |
| 8,652,204 B2 | 2/2014 | Quill et al. |
| 8,663,314 B2 | 3/2014 | Wood et al. |
| 8,753,407 B2 | 6/2014 | Nguyen |
| 8,834,558 B2 | 9/2014 | Nissl |
| 8,979,892 B2 | 3/2015 | Shalev |
| 8,986,368 B2 | 3/2015 | Gill et al. |
| 9,005,275 B2 | 4/2015 | Cassivi et al. |
| 9,138,336 B2 | 9/2015 | Carman et al. |
| 9,179,921 B1 | 11/2015 | Morris |
| 9,510,959 B2 | 12/2016 | Shoham et al. |
| 10,064,626 B2 | 9/2018 | Celermajer et al. |
| 10,314,726 B2 | 6/2019 | Hollyer et al. |
| 10,426,592 B2 | 10/2019 | Folan et al. |
| 10,470,910 B2 | 11/2019 | Folan et al. |
| 2001/0010012 A1 | 7/2001 | Edwin et al. |
| 2002/0133224 A1* | 9/2002 | Bajgar .............. A61L 31/16 623/1.39 |
| 2005/0090888 A1 | 4/2005 | Hines et al. |
| 2005/0113904 A1 | 5/2005 | Shank et al. |
| 2006/0095124 A1 | 5/2006 | Benz et al. |
| 2007/0255394 A1 | 11/2007 | Ryan |
| 2010/0063579 A1 | 3/2010 | An |
| 2010/0256754 A1 | 10/2010 | Styrc |
| 2010/0298631 A1 | 11/2010 | Stack et al. |
| 2011/0022151 A1 | 1/2011 | Shin et al. |
| 2011/0093002 A1 | 4/2011 | Rucker et al. |
| 2011/0190905 A1 | 8/2011 | Behan |
| 2011/0282461 A1 | 11/2011 | Shin et al. |
| 2012/0046684 A1 | 2/2012 | Evans et al. |
| 2012/0150274 A1 | 6/2012 | Shalev et al. |
| 2013/0150950 A1 | 6/2013 | Schlick et al. |
| 2014/0243965 A1 | 8/2014 | Benson et al. |
| 2014/0343683 A1 | 11/2014 | Jeon et al. |
| 2015/0045881 A1 | 2/2015 | Lim |
| 2015/0119974 A1 | 4/2015 | Rothstein |
| 2015/0320578 A1 | 11/2015 | Bui et al. |
| 2016/0058585 A1 | 3/2016 | Seddon et al. |
| 2016/0120638 A1 | 5/2016 | Michalak |
| 2016/0175122 A1* | 6/2016 | O'Shaughnessy ........ A61F 2/04 623/23.7 |
| 2018/0125633 A1 | 5/2018 | Fikfak et al. |
| 2018/0125682 A1 | 5/2018 | Folan et al. |
| 2018/0280167 A1 | 10/2018 | Folan et al. |
| 2019/0240009 A1 | 8/2019 | Benson et al. |
| 2019/0321204 A1 | 10/2019 | Folan et al. |
| 2019/0388251 A1 | 12/2019 | Bortone |

FOREIGN PATENT DOCUMENTS

| | | |
|---|---|---|
| EP | 2803338 A1 | 11/2014 |
| KR | 20000056338 A | 9/2000 |

OTHER PUBLICATIONS

International Search Report and Written Opinion dated Jul. 2, 2021 for International Application No. PCT/US2020/066112.

* cited by examiner

RADIAL ADJUSTING SELF-EXPANDING STENT WITH ANTI-MIGRATION FEATURES

CROSS REFERENCE TO RELATED APPLICATIONS

The present application claims the benefit of and priority to U.S. Provisional patent Application Ser. No. 62/967,755, filed on Jan. 30, 2020, the disclosure of which is incorporated herein by reference.

TECHNICAL FIELD

The disclosure is directed to a stent and a method for forming a stent. More particularly, the disclosure is directed to a self-expanding stent having anti-migration features and a method of forming a self-expanding stent having anti-migration features.

BACKGROUND

A stent may be configured to be positioned in a body lumen for a variety of medical applications. For example, a stent may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. In some cases, a stent may include anti-migration features in order to help anchor the stent in place in whichever body lumen the stent is placed. In some instances, forming these anti-migration features may be difficult to do accurately and repeatedly. Of the known medical devices and methods of manufacture, each has certain advantages and disadvantages. There is an ongoing need to provide alternative medical devices and methods of manufacture.

SUMMARY

In one example, an esophageal stent may comprise: an expandable framework having a first end, a second end, and a central longitudinal axis extending from the first end to the second end, the expandable framework being configured to expand from a radially collapsed configuration to a radially expanded configuration; and a polymeric outer sleeve disposed radially outward of and spaced apart from a body region of the expandable framework. The expandable framework may include a plurality of anti-migration supports extending radially outward from the body region of the expandable framework toward the polymeric outer sleeve.

In addition or alternatively to any example disclosed herein, the expandable framework is configured to self-expand from the radially collapsed configuration to the radially expanded configuration when unconstrained.

In addition or alternatively to any example disclosed herein, the plurality of anti-migration supports extends radially outward from the body region at an oblique angle to the central longitudinal axis.

In addition or alternatively to any example disclosed herein, the plurality of anti-migration supports is angled toward the second end of the expandable framework.

In addition or alternatively to any example disclosed herein, the oblique angle is greater than about 45 degrees and less than 90 degrees.

In addition or alternatively to any example disclosed herein, the expandable framework may include a first flared region proximate the first end and a second flared region proximate the second end. The body region may extend from the first flared region to the second flared region.

In addition or alternatively to any example disclosed herein, the expandable framework is encapsulated within a polymeric covering.

In addition or alternatively to any example disclosed herein, the plurality of anti-migration supports is a plurality of anti-migration loops each hingedly attached to the expandable framework at a base of the anti-migration loops.

In addition or alternatively to any example disclosed herein, an esophageal stent may comprise: an expandable framework having a first end, a second end, and a central longitudinal axis extending from the first end to the second end, the expandable framework being configured to expand from a radially collapsed configuration to a radially expanded configuration; and a polymeric outer sleeve disposed radially outward of and spaced apart from a body region of the expandable framework. The expandable framework may include a plurality of interwoven filaments. At least a portion of the plurality of interwoven filaments may extend radially outward beyond an outer diameter of the body region to form anti-migration loops. The anti-migration loops may extend from the body region at a first angle. A base of each of the anti-migration loops may form a hinge portion such that the anti-migration loops are elastically deflectable from the first angle to a second angle less than the first angle. The anti-migration loops may extend radially outward from the body region to the polymeric outer sleeve.

In addition or alternatively to any example disclosed herein, the anti-migration loops are configured to deflect radially inward at the base when subjected to a radially inward force.

In addition or alternatively to any example disclosed herein, the expandable framework is configured to maintain a constant inner diameter when the anti-migration loops are subjected to the radially inward force.

In addition or alternatively to any example disclosed herein, an axial force applied to the expandable framework in a direction toward the second end in situ is transmitted radially outward through the anti-migration loops.

In addition or alternatively to any example disclosed herein, the expandable framework may include a first flared region proximate the first end and a second flared region proximate the second end. The body region may extend from the first flared region to the second flared region. The first flared region and the second flared region may have an outer diameter in the radially expanded configuration, and the outer diameter of the body region may be less than the outer diameter of the first flared region and the second flared region. An outer radial extent of the plurality of anti-migration loops in the radially expanded configuration may be substantially equal to the outer diameter of the first flared region and the second flared region.

In addition or alternatively to any example disclosed herein, the first angle is an oblique angle.

In addition or alternatively to any example disclosed herein, an esophageal stent may comprise: a metallic expandable framework having a first end, a second end, and a central longitudinal axis extending from the first end to the second end, the expandable framework being configured to self-expand from a radially collapsed configuration to a radially expanded configuration when unconstrained; and a polymeric outer sleeve disposed radially outward of the expandable framework. The expandable framework may include a first flared region proximate the first end, a second flared region proximate the second end, and a body region extending from the first flared region to the second flared region. The expandable framework may be encapsulated within a polymeric covering. The expandable framework may include a plurality of anti-migration loops each hingedly attached to the expandable framework at a base of the plurality of anti-migration loops. The plurality of anti-migration loops may be heat set to be biased toward the expanded configuration.

In addition or alternatively to any example disclosed herein, the polymeric covering and the polymeric outer sleeve are fixedly attached together at the first flared region and the second flared region.

In addition or alternatively to any example disclosed herein, the plurality of anti-migration loops spaces the polymeric outer sleeve apart from the body region.

In addition or alternatively to any example disclosed herein, the body region maintains a fixed inner diameter when subjected to a radially inward force up to about 5 Newtons.

In addition or alternatively to any example disclosed herein, wherein the plurality of anti-migration loops is configured to deflect radially inward toward the body region at the base when subjected to a radially inward force less than about 5 Newtons.

In addition or alternatively to any example disclosed herein, each of the plurality of anti-migration loops is formed of an arcuate segment of a filament of the expandable framework, wherein the arcuate segment of the filament forming the anti-migration loop is located between first and second segments of the filament helically extending around the expandable framework interwoven with other filaments of the expandable framework.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The invention may be more completely understood in consideration of the following detailed description in connection with the accompanying drawings, in which.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/ manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Figure 1:
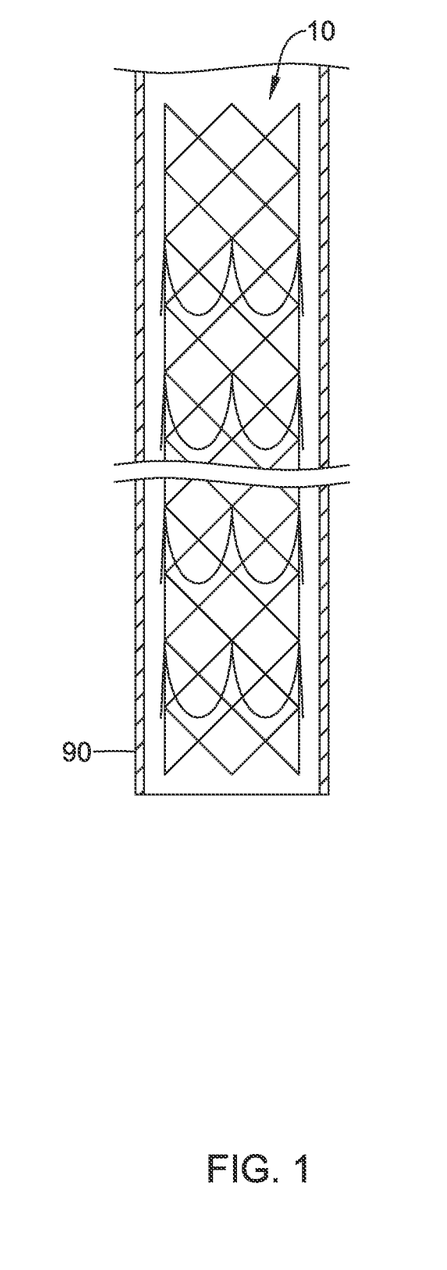
FIG. 1 is a schematic partial cross-sectional view of an esophageal stent disposed within a delivery sheath in a radially collapsed configuration.

FIG. 1 schematically illustrates an esophageal stent 10 disposed within a delivery sheath 90. To improve clarity, some features of the esophageal stent 10 disclosed herein are not shown in FIG. 1, such as a polymeric covering 22 and/or a polymeric outer sleeve 30 (e.g., FIGS. 5-8). The delivery sheath 90 may radially constrain the esophageal stent 10 in a radially collapsed configuration. As shown in FIG. 1, the esophageal stent 10 may be disposed within a distal portion of a lumen of the delivery sheath 90. The delivery sheath 90 is illustrated with a distal opening in communication with the lumen. Other configurations are also contemplated. In some embodiments, delivery of the esophageal stent 10 may involve retracting the delivery sheath 90 relative to the esophageal stent 10 or advancement of the esophageal stent 10 out of the delivery sheath 90. In some embodiments, an internal member (not shown) may be disposed within the lumen of the delivery sheath 90. For example, the internal member may be configured to hold the esophageal stent 10 as the delivery sheath 90 is retracted or the internal member may be configured to push or advance the esophageal stent 10 out of the distal opening of the delivery sheath 90. Other configurations are also contemplated.

Figure 2:
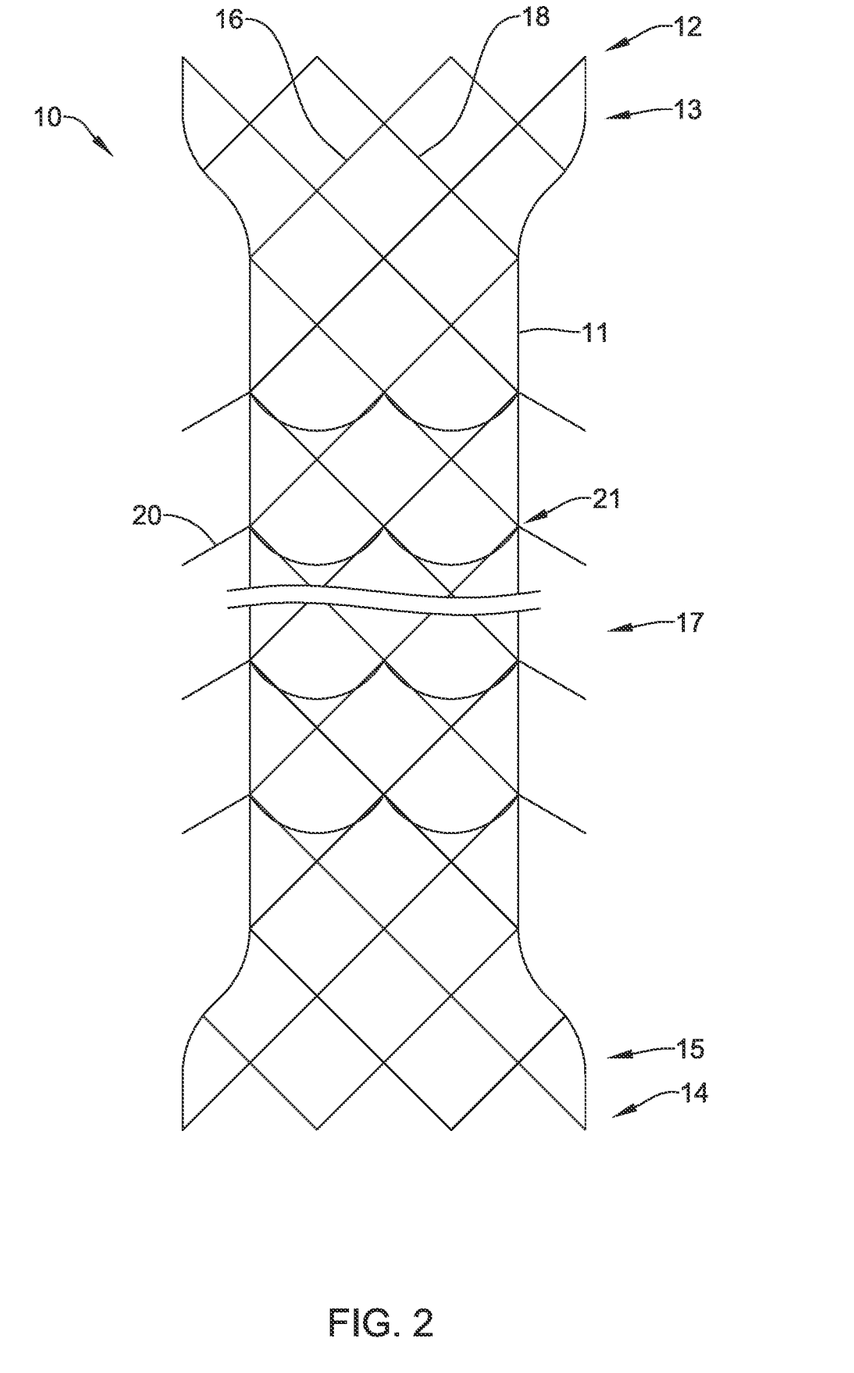
FIG. 2 illustrates selected aspects of an expandable framework of an esophageal stent in a radially expanded configuration.

As seen in FIG. 2, the esophageal stent 10 may include an expandable framework 11 having a first end 12, a second end 14 and a lumen extending therethrough. In at least some embodiments, the expandable framework 11 may be and or define a generally tubular structure. The esophageal stent 10 and/or the expandable framework 11 may include a central longitudinal axis extending from the first end 12 to the second end 14. The expandable framework 11 may be configured to expand and/or self-expand from the radially collapsed configuration (e.g., FIG. 1) to a radially expanded configuration (e.g., FIG. 2). In some embodiments, the expandable framework 11 may be configured to self-expand from the radially collapsed configuration to the radially expanded configuration when unconstrained (e.g., radially and/or axially unconstrained). In some embodiments, the expandable framework 11 in the radially collapsed configuration may be elongated and/or longer than in the radially expanded configuration. As such, in some embodiments, when the expandable framework 11 is radially expanded, the expandable framework 11 may shorten axially.

In at least some embodiments, the expandable framework 11 may include a first flared region 13 proximate the first end 12 and a second flared region 15 proximate the second end 14. The expandable framework 11 may include a body region 17. In some embodiments, the body region 17 may extend from the first flared region 13 to the second flared region 15. In some embodiments, the first flared region 13 and/or the second flared region 15 have an outer diameter in the radially expanded configuration, wherein an outer diameter of the body region 17 is less than the outer diameter of the first flared region 13 and/or the second flared region 15.

In some embodiments, the expandable framework 11 may include a plurality of interwoven filaments. In some embodiments, the plurality of interwoven filaments may include a plurality of first filaments 16 each extending in a first helical path around the central longitudinal axis in a first direction from the first end 12 toward and/or to the second end 14. In some embodiments, the first direction may be clockwise. In some embodiments, the plurality of interwoven filaments may include a plurality of second filaments 18 each extending in a second helical path around the central longitudinal axis in a second direction from the first end 12 toward and/or to the second end 14. In some embodiments, the second direction may be opposite the first direction. In some embodiments, the second direction may be counterclockwise. In some embodiments, the plurality of first filaments 16 may be interwoven with the plurality of second filaments 18, such as when forming a braided stent (e.g., FIG. 3). Alternatively, in some embodiments, the expandable framework 11 may be a monolithic structure including a plurality of interconnected struts and/or a single filament interwoven with itself, such as when forming a knitted stent (e.g., FIG. 4). In some embodiments, the expandable framework 11 may be cut from a tubular member, using various means known in the art (e.g., laser, machining, etching, chemical dissolution, etc.). In at least some embodiments, the expandable framework 11 may be formed from a metallic material, a polymeric material, a composite material, combinations thereof, etc. Some examples of suitable but non-limiting materials for the expandable framework 11 and/or elements or components thereof are described below.

Figure 3:
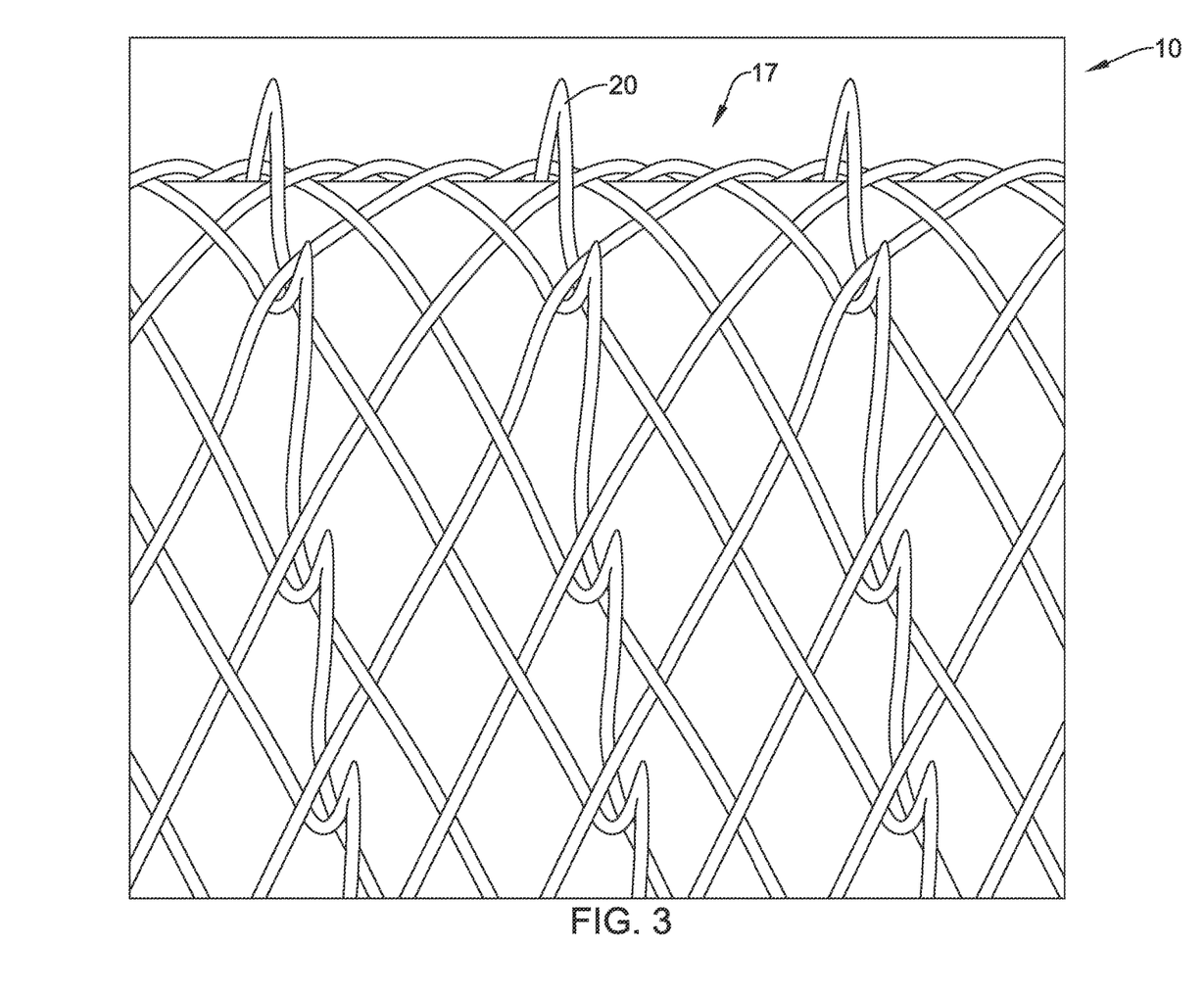
FIGS. 3-4 illustrate some examples of the formation of the plurality of anti-migration supports or loops.
Figure 4:
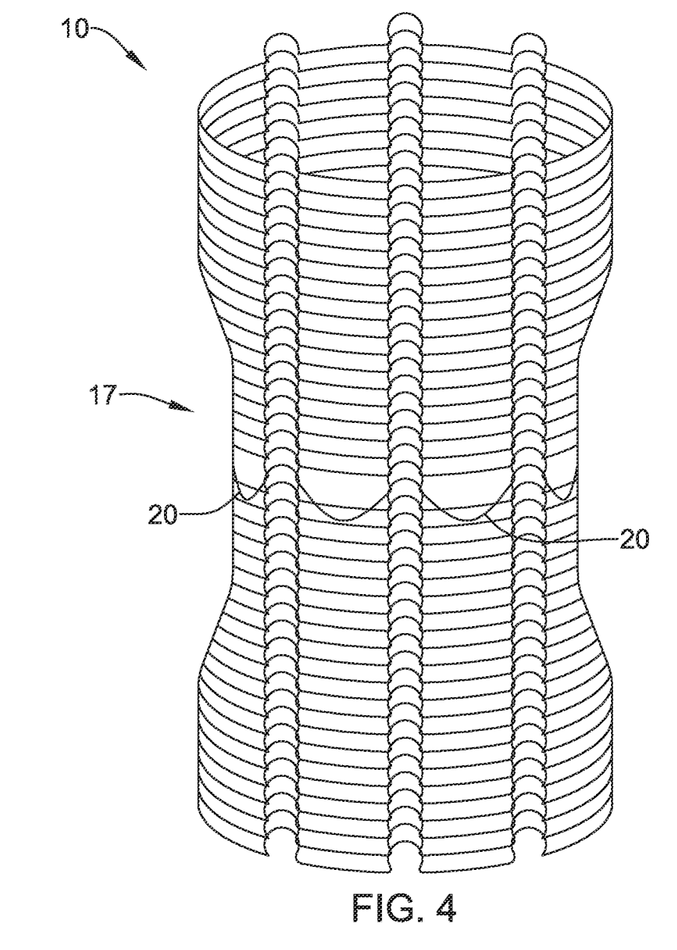

The expandable framework 11 may include a plurality of anti-migration supports 20 (e.g., arms, struts, projections, etc.) extending radially outward from the body region 17 of the expandable framework 11. In some embodiments, the plurality of anti-migration supports 20 may be a plurality of anti-migration loops each hingedly and/or pivotably attached to the expandable framework 11 at a base 21 of the plurality of anti-migration loops and/or the plurality of anti-migration supports 20. The plurality of anti-migration supports 20 and/or the anti-migration loops may extend from the base 21 toward the second end 14 of the expandable framework 11. In some embodiments, at least a portion of the plurality of interwoven filaments may extend radially outward beyond the outer diameter of the body region 17 of the esophageal stent 10 to form the plurality of anti-migration supports 20 and/or the anti-migration loops, as seen in the examples of FIGS. 3 and 4. Other configurations and/or examples are also contemplated. In at least some embodiments, the plurality of anti-migration supports 20 and/or the anti-migration loops may be formed with the expandable framework 11 as a single monolithic structure. For instance, the expandable framework 11 may be formed of a plurality of interwoven (e.g., braided) filaments. In some instances, the interwoven filaments forming the expandable framework 11 may extend helically around the expandable framework 11 and cross over and/or under filaments extending helically in an opposite direction. Each of the plurality of anti-migration loops may be formed of an integral segment, such as an arcuate segment, of a filament of the expandable framework 11, wherein the arcuate segment of the filament forming the anti-migration loop is located between first and second segments of the filament helically extending around the expandable framework 11 interwoven with other filaments of the expandable framework 11.

The plurality of anti-migration supports 20 and/or the anti-migration loops may be spaced apart from one another longitudinally along the length of the body region 17 of the expandable framework 11 and/or circumferentially around the circumference of the body region 17 of the expandable framework 11. For instance, the body region 17 of the expandable framework 11 may include 2 or more, 3 or more, 4 or more, 5 or more, or 6 or more longitudinal rows, helical rows and/or circumferential rows of anti-migration supports 20 and/or anti-migration loops, with 5 or more, 8 or more, 10 or more, 14 or more, or 20 or more anti-migration supports 20 and/or anti-migration loops in each row. In the figures, the plurality of anti-migration supports 20 in a given row are illustrated as being aligned with the plurality of anti-migration supports 20 in adjacent rows, but this is not strictly necessary in all embodiments. For example, the plurality of anti-migration supports 20 may be staggered or offset from each other in any given pair of adjacent rows.

In some embodiments, the plurality of anti-migration supports 20 and/or the anti-migration loops may extend radially outward of and/or from the body region 17 of the expandable framework 11 about 2.0 millimeters (mm), about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.5 mm, about 8.0 mm, or another suitable distance, in the expanded configuration. In some exemplary embodiments, the plurality of anti-migration supports 20 and/or the anti-migration loops may extend radially outward from the body region 17 about 4.0 mm to about 6.0 mm in the expanded configuration.

Figure 5:
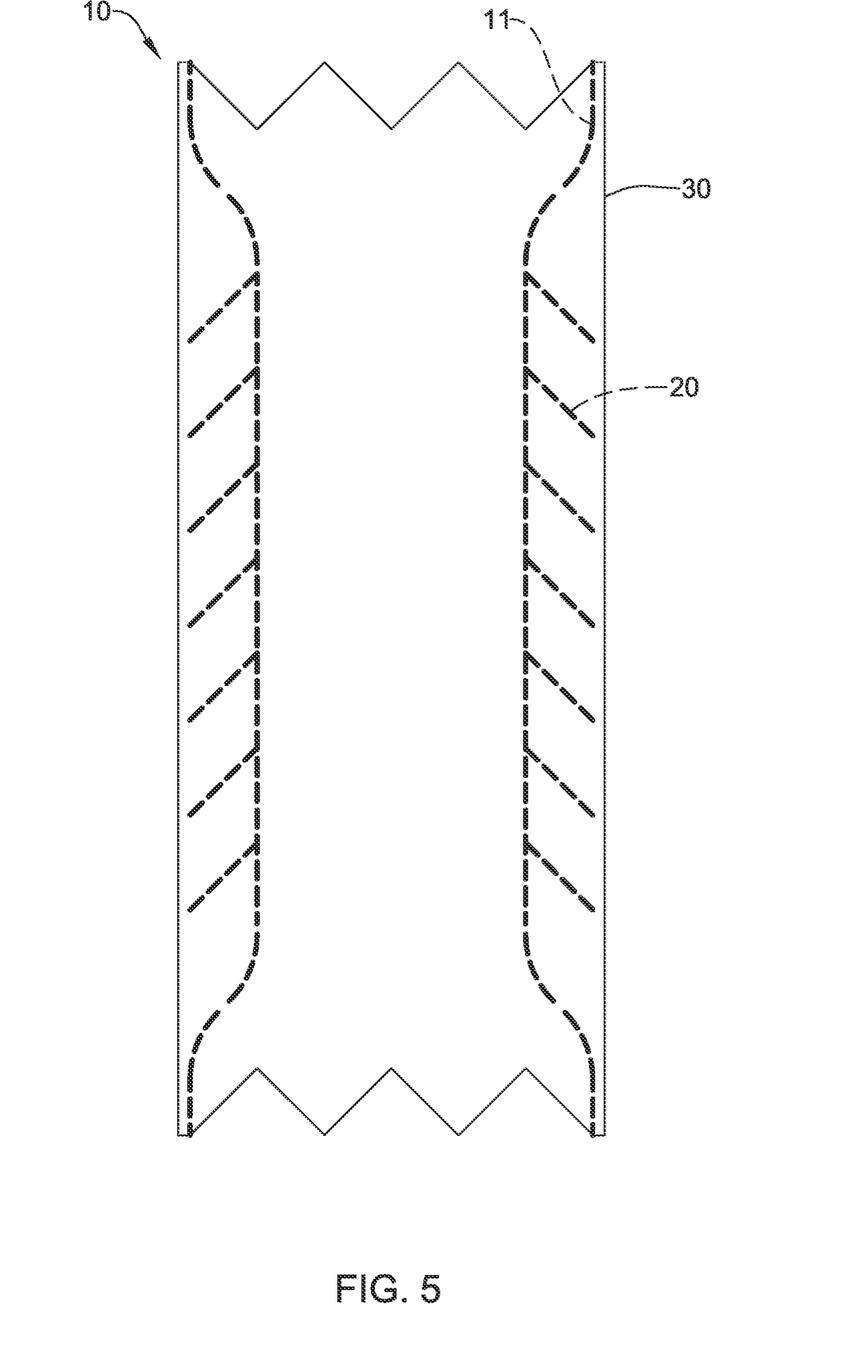
FIG. 5 illustrates selected aspects of an esophageal stent.
Figure 6:
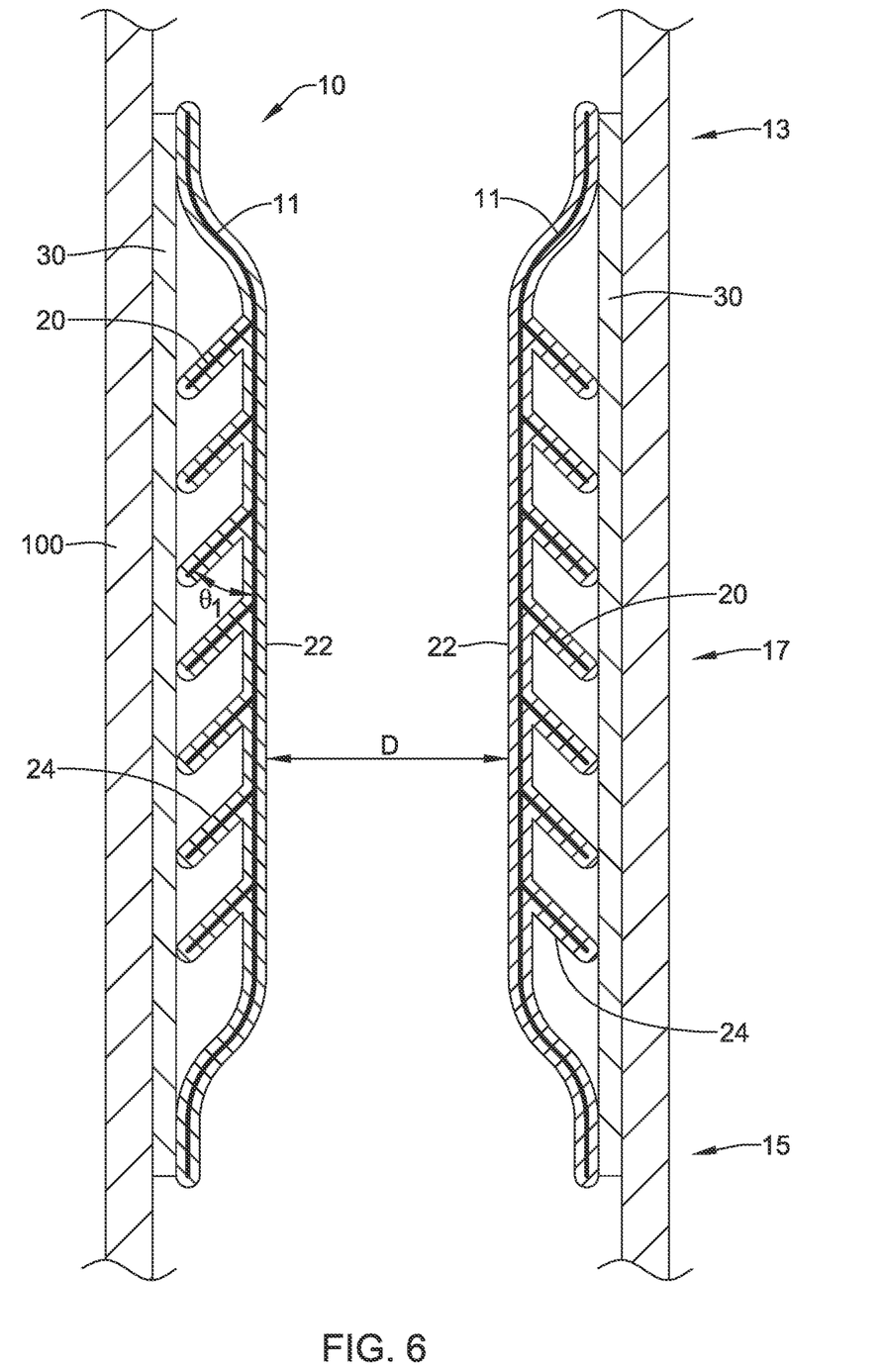
FIG. 6 is a schematic partial cross-sectional view of an esophageal stent disposed within a body lumen in a radially expanded configuration.

In some embodiments, the esophageal stent 10 may be a covered stent. In some embodiments, the esophageal stent 10 may include a polymeric outer sleeve 30 disposed radially outward of the expandable framework 11. In some embodiments, the polymeric outer sleeve 30 may be spaced apart from at least the body region 17 of the expandable framework 11, as seen in FIG. 5. It should be noted that FIGS. 5-8 are merely illustrative, and the expandable framework 11 may include more or fewer anti-migration supports and/or rows of anti-migration supports than shown. In some embodiments, the plurality of anti-migration supports 20 and/or the anti-migration loops may extend radially outward from the body region 17 of the expandable framework 11 toward and/or to the polymeric outer sleeve 30. In some embodiments, the plurality of anti-migration supports 20 and/or the anti-migration loops spaces the polymeric outer sleeve 30 apart from at least the body region 17 of the expandable framework 11, as seen in FIG. 6, which illustrates the esophageal stent 10 disposed within a body lumen 100 (e.g., the esophagus) in partial cross-section. In some embodiments, the polymeric outer sleeve 30 may be attached to the expandable framework 11 at the first flared region 13 and/or the second flared region 15.

In some embodiments, the expandable framework 11 may be encapsulated within a polymeric covering 22. The polymeric covering 22 may span interstices in the expandable framework 11 and/or may define a lumen extending through the esophageal stent 10 and/or the expandable framework 11. In some embodiments, the polymeric covering 22 may encapsulate, be disposed on and/or attached to the plurality of first filaments and the plurality of second filaments. In some embodiments, the polymeric covering 22 may span interstices between adjacent filaments of the plurality of first filaments and the plurality of second filaments. In some instances, the polymeric covering 22 may fully cover the expandable framework 11 along the entire length and circumference of the expandable framework 11.

In some embodiments, the polymeric covering 22 and/or the polymeric outer sleeve 30 may be impervious to fluids, debris, and/or tissue ingrowth. In some embodiments, the polymeric covering 22 and/or the polymeric outer sleeve 30 may extend along the body region 17 of the expandable framework 11 from the first flared region 13 to the second flared region 15. In some embodiments, the polymeric covering 22 and/or the polymeric outer sleeve 30 may extend along an entire length and circumference of the esophageal stent 10 and/or the expandable framework 11 from the first end 12 to the second end 14. In some embodiments, the polymeric covering 22 may be disposed on an inner surface of the body region 17, an outer surface of the body region 17, both the inner surface and the outer surface of the body region 17, or the body region 17 may be embedded within the polymeric covering 22 with the plurality of anti-migration supports 20 and/or the anti-migration loops protruding radially outward from the polymeric covering 22. Other configurations are also contemplated.

In some embodiments, the body region 17, the first flared region 13, and/or the second flared region 15 may be encapsulated within a first portion of the polymeric covering 22. In some embodiments, the plurality of anti-migration supports 20 and/or the anti-migration loops may be encapsulated within a second portion 24 of the polymeric covering 22. In some embodiments, the entire expandable framework 11 may be encapsulated within the polymeric covering 22. In some embodiments, the first portion of the polymeric covering 22 and the second portion 24 of the polymeric covering 22 may be formed as a single monolithic structure from a single material. In some embodiments, the first portion of the polymeric covering 22 may be fixedly attached to the second portion 24 of the polymeric covering 22 at and/or adjacent the base 21 of the plurality of anti-migration supports 20 and/or the anti-migration loops. In some embodiments, the polymeric covering 22 and the polymeric outer sleeve 30 may be fixedly attached together at the first flared region 13 and/or the second flared region 15. In some embodiments, the second portion 24 of the polymeric covering 22 may be fixedly attached to the polymeric outer sleeve 30 at a radially outermost extent of the plurality of anti-migration supports 20 and/or the anti-migration loops and/or the second portion 24 of the polymeric covering 22 disposed thereon. In some embodiments, the polymeric outer sleeve 30 may be a third portion of the polymeric covering 22. In some embodiments, the first portion of the polymeric covering 22, the second portion 24 of the polymeric covering 22, and the third portion of the polymeric covering 22 (e.g., the polymeric outer sleeve 30) may be formed as a single monolithic structure from a single material.

In some embodiments, the polymeric covering 22 (and/or the polymeric outer sleeve 30) may be formed having a single Shore hardness. In some embodiments, each portion of the polymeric covering 22 may have a different Shore hardness. In some embodiments, the first portion of the polymeric covering 22 may have a different Shore hardness than the second portion 24 of the polymeric covering 22 and/or the third portion of the polymeric covering 22 (e.g., the polymeric outer sleeve 30). In some embodiments, the Shore hardness of the second portion 24 of the polymeric covering 22 may be higher than the Shore hardness of the first portion of the polymeric covering 22. Various combinations of Shore hardness (e.g., same, similar, and/or different) among these portions of the polymeric covering 22 are also contemplated.

In some embodiments, a plurality of spaces may be disposed between the polymeric covering 22 and the polymeric outer sleeve 30. In some embodiments, a plurality of spaces may be disposed between adjacent second portions 24 of the polymeric covering 22 (e.g., between adjacent anti-migration supports 20 and/or between adjacent anti-migration loops). In some embodiments, the plurality of spaces may be connected to each other between the polymeric covering 22 and the polymeric outer sleeve 30 to define a collective space therebetween. In some embodiments, the plurality of spaces may be a plurality of discrete cells or chambers. Other configurations, including but not limited to combinations of these configurations, are also contemplated.

The plurality of anti-migration supports 20 and/or the anti-migration loops may extend radially outward from the body region 17 at a first angle $\theta_1$ relative to the body region 17 and/or the central longitudinal axis when not subjected to an external force such as a peristaltic force, as seen in FIG. 6. The plurality of anti-migration supports 20 and/or the anti-migration loops may be angled toward the second end 14 of the expandable framework 11. In some embodiments, the first angle $\theta_1$ may be an oblique angle. In some embodiments, the oblique angle may be greater than about 30 degrees and less than 90 degrees, greater than about 45 degrees and less than 90 degrees, greater than about 60 degrees and less than 90 degrees, or another angle suitable for and/or consistent with the characteristics described herein.

Figure 7:
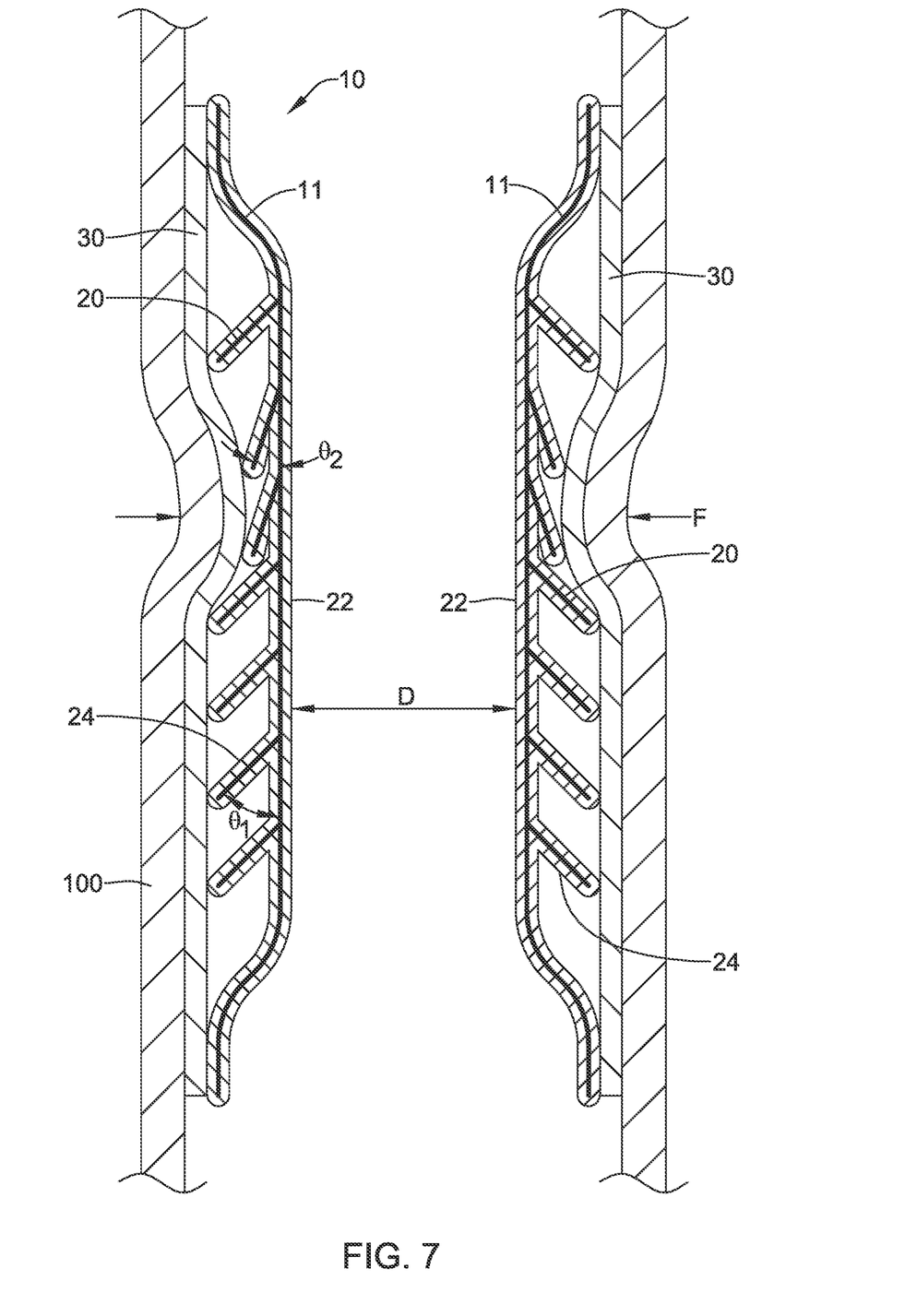
FIGS. 7-8 illustrate selected aspects of the esophageal stent being subjected to peristaltic forces within the body lumen.
Figure 8:
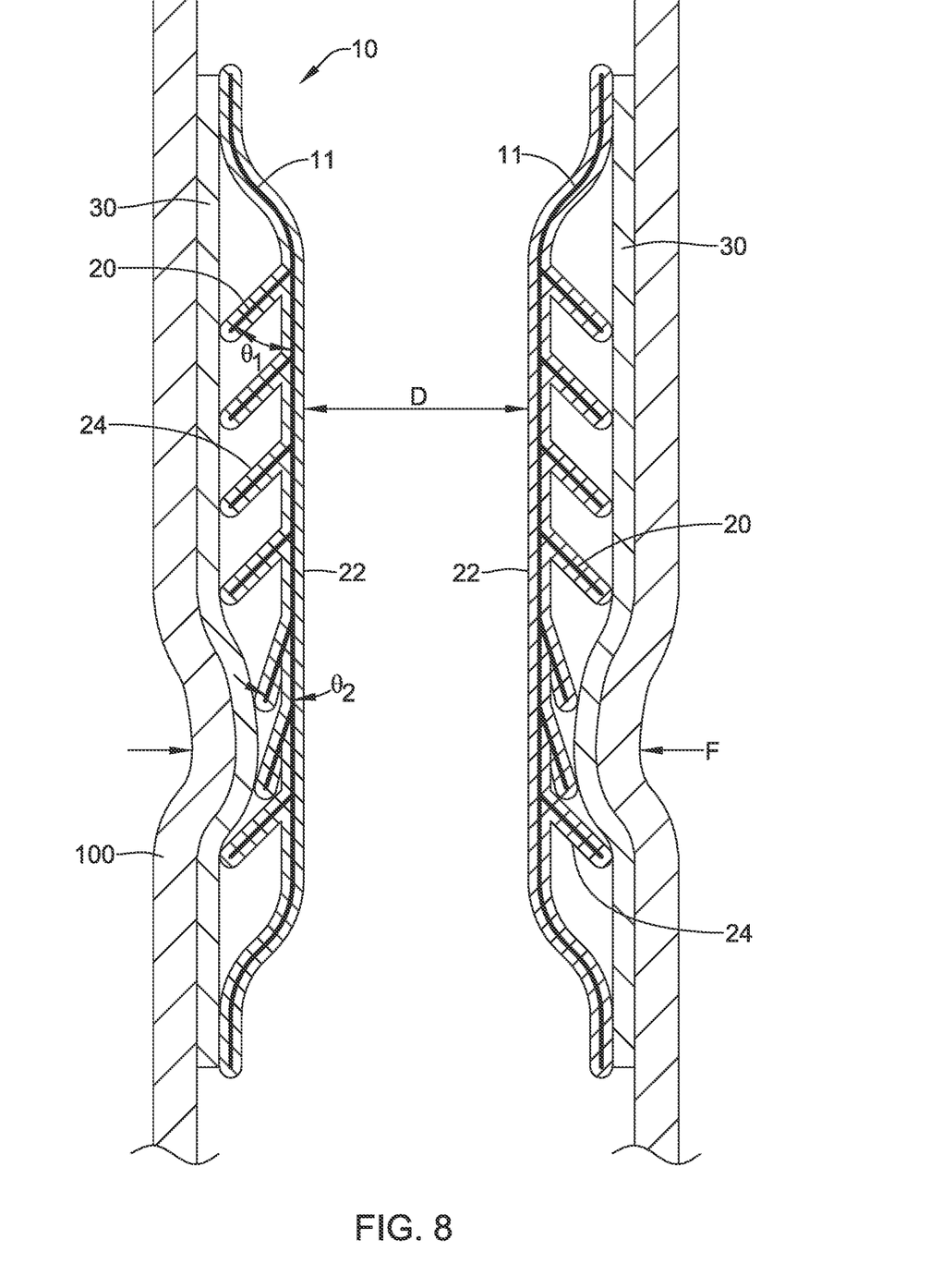

In some embodiments, a base 21 of each of the plurality of anti-migration supports 20 and/or the anti-migration loops may form a hinge portion such that the plurality of anti-migration supports 20 and/or the anti-migration loops may be elastically deflectable at the base 21 and/or the hinge portion from the first angle $\theta_1$ to a second angle $\theta_2$ less than the first angle $\theta_1$ when subjected to an external force, such as a radially inwardly directed peristaltic force (e.g., FIGS. 7 and 8). The second angle $\theta_2$ may be 10 or more degrees less than the first angle $\theta_1$, 15 or more degrees less than the first angle $\theta_1$, 20 or more degrees less than the first angle $\theta_1$, 30 or more degrees less than the first angle $\theta_1$, or 45 or more degrees less than the first angle $\theta_1$, for example.

In some embodiments, the plurality of anti-migration supports 20 and/or the anti-migration loops may be heat set (e.g., during manufacturing) to be self-biased toward the radially expanded configuration in which the anti-migration supports 20 and/or the anti-migration loops assume the first angle $\theta_1$. Similarly, the esophageal stent 10 and/or the expandable framework 11 may be heat set to be self-biased toward the radially expanded configuration. In the radially expanded configuration, the expandable framework 11 and/or the body region 17 may define an inner diameter D defining the lumen extending therethrough.

In use, the esophageal stent 10 may be disposed within the body lumen 100 in the radially expanded configuration, as shown in FIG. 6. In at least some embodiments, placement of the esophageal stent 10 may be via conventional means known in the art. The polymeric outer sleeve 30 may be disposed against and/or in contact with an inner surface of the body lumen 100. The polymeric outer sleeve 30 may prevent tissue ingrowth into the esophageal stent 10, thereby facilitating easier removal of the esophageal stent 10 from the body lumen 100 at a later time. The first flared region 13 and/or the second flared region 15 may be self-biased toward the radially expanded configuration, and in the radially expanded configuration, may exert a radially outward force against the inner surface of the body lumen 100.

Since the expandable framework 11 may be encapsulated within the polymeric covering 22, a bolus may be able to easily pass through the lumen of the esophageal stent 10. In an instance where the bolus does not pass easily through the lumen of the esophageal stent 10, axial forces may be exerted upon and/or applied to the esophageal stent 10 and/or the expandable framework 11 in a downstream direction toward the second end. Since the plurality of anti-migration supports 20 and/or the anti-migration loops are hingedly and/or pivotably attached to the expandable framework 11 at the base 21 of the plurality of anti-migration supports 20 and/or the anti-migration loops, axial forces applied to the esophageal stent 10 and/or the expandable framework 11 may cause the plurality of anti-migration supports 20 and/or the anti-migration loops, which are substantially rigid in a direction parallel to the central longitudinal axis between the base 21 and the radially outermost extent, to hinge or pivot radially outward at the base 21, thereby exerting and/or increasing a radially outward force exerted on the body lumen 100 due to the plurality of anti-migration supports 20 and/or the anti-migration loops being wedged between the inner surface of the body lumen 100 and the body region 17 of the expandable framework 11, which may resist radially inward collapse due to stent construction, heat setting, self-bias, and/or other factors. As such, axial forces may be transmitted radially outward through the plurality of anti-migration supports 20 and/or the anti-migration loops to the inner surface of the body lumen 100, thereby increasing an anchoring force and/or increasing resistance of the esophageal stent 10 to axial migration within the body lumen 100.

Some body lumens may exert peristaltic forces or motion on and/or against a stent disposed therein. The peristaltic forces or motion may include an axial component. In some instances, repeated exposure to the peristaltic forces or motion may cause a stent to migrate axially downstream within the body lumen. Migration is typically undesirable as placement is usually intended to treat a specific area or location within the body lumen. FIGS. 7-8 illustrate peristaltic forces or motion passing by the esophageal stent 10 disposed within the body lumen 100. As may be seen in the figures, the peristaltic forces or motion may apply a radially inward force F against the esophageal stent 10. The plurality of anti-migration supports 20 and/or the anti-migration loops may be configured to elastically deflect radially inward at the base 21 from a first angle $\theta_1$ to a second angle $\theta_2$ less than the first angle $\theta_1$ while the body region 17 of the expandable framework 11 maintains a constant inner diameter. As the radially inward force F passes and/or is relieved, the plurality of anti-migration supports 20 and/or the anti-migration loops may elastically return to the first angle $\theta_1$, as seen in FIG. 8. The deflection characteristics of the plurality of anti-migration supports 20 and/or the anti-migration loops may reduce the axial component of the peristaltic forces or motion on the esophageal stent 10, while maintaining anchoring and/or anti-migration forces on and/or against the inner surface of the body lumen 100, thereby preventing axial migration of the esophageal stent 10 within the body lumen 100.

In some embodiments, the plurality of anti-migration supports 20 and/or the anti-migration loops may be configured to deflect radially inward at the base 21 and/or the hinge portion when subjected to a radially inward force F, such as a radially inwardly directed peristaltic force, as seen in FIGS. 7-8. In some embodiments, the plurality of anti-migration supports 20 and/or the anti-migration loops may be configured to deflect radially inward toward the body region 17 at the base 21 and/or the hinge portion when subjected to a radially inward force F greater than about 0.5 Newtons and less than about 5.0 Newtons, greater than about 1.0 Newton and less than about 4 Newtons, greater than about 2.0 Newtons and less than about 3.0 Newtons, about 2.4 Newtons, or another suitable amount of force. For example, the plurality of anti-migration supports 20 and/or the anti-migration loops may be configured to deflect at the base 21 and/or the hinge portion such that a radially outermost extent of the plurality of anti-migration supports 20 and/or the anti-migration loops is deflected, moved, and/or translated toward the second end 14 while moving closer to the central longitudinal axis of the expandable framework 11 when the plurality of anti-migration supports 20 and/or the anti-migration loops is subjected to a radially inward force F, thereby changing orientation of the plurality of anti-migration supports 20 and/or the anti-migration loops from the first angle $\theta_1$ to the second angle $\theta_2$.

In some embodiments, the expandable framework 11 and/or the body region 17 of the expandable framework 11 is configured to maintain a substantially constant and/or fixed inner diameter D when the plurality of anti-migration supports 20 and/or the anti-migration loops are subjected to the radially inward force F. In some embodiments, when the plurality of anti-migration supports 20 and/or the anti-migration loops are subjected to the radially inward force F, the expandable framework 11 and/or the body region 17 of the expandable framework 11 may be configured to maintain the inner diameter D at at least 90% of its original inner diameter D (e.g., when the radially inward force F is absent), at at least 95% of its original inner diameter D (e.g., when the radially inward force F is absent), at at least 97% of its original inner diameter D (e.g., when the radially inward force F is absent), and/or at at least 99% of its original inner diameter D (e.g., when the radially inward force F is absent). Other configurations are also contemplated.

In some embodiments, the expandable framework 11 and/or the body region 17 of the expandable framework 11 is configured to maintain a substantially constant and/or fixed inner diameter D when the plurality of anti-migration supports 20 and/or the anti-migration loops are subjected to the radially inward force F up to about 5.0 Newtons. For example, a radially inward force F up to about 5.0 Newtons sufficient to deflect the plurality of anti-migration supports 20 and/or the anti-migration loops will have substantially no effect on the shape and/or form of the body region 17 and/or the expandable framework 11. Other configurations are also contemplated. When the radially inward force F is removed, the plurality of anti-migration supports 20 and/or the anti-migration loops may elastically return to the first angle $\theta_1$.

In some embodiments, the plurality of anti-migration supports 20 and/or the anti-migration loops may be substantially rigid from the base 21 and/or the hinge portion to the radially outermost extent of the plurality of anti-migration supports 20 and/or the anti-migration loops in a direction parallel to the central longitudinal axis. For example, the plurality of anti-migration supports 20 and/or the anti-migration loops may be configured to deflect at the base 21 and/or the hinge portion but may be prevented from deflecting toward the first end 12 or the second end 14 at a location between the base 21 and/or the hinge portion and the radially outermost extent of the plurality of anti-migration supports 20 and/or the anti-migration loops. As such, in some embodiments, an axial force applied to the expandable framework 11 in a direction toward the second end 14 in situ may be transmitted radially outward through the plurality of anti-migration supports 20 and/or the anti-migration loops. Since the plurality of anti-migration supports 20 and/or the anti-migration loops will not deflect or bend along their length (under expected in situ forces of less than 5.0 Newtons), the hinging and/or pivoting motion at the base 21 will cause additional radially outward force to be applied to a wall of a lumen, thereby increasing anchoring forces and reducing and/or preventing axial migration of the esophageal stent 10 in situ.

In some embodiments, the plurality of anti-migration supports 20 and/or the anti-migration loops extending radially outward from the body region 17 of the esophageal stent 10 and/or the expandable framework 11 may form a circumferential row of the plurality of anti-migration supports 20 and/or the anti-migration loops extending around the body region 17 of the expandable framework 11. In some embodiments, the plurality of anti-migration supports 20 and/or the anti-migration loops within the circumferential row of the plurality of anti-migration supports 20 and/or the anti-migration loops may be axially and/or circumferentially aligned at a common axial location along the central longitudinal axis of the esophageal stent 10 and/or the expandable framework 11.

In some embodiments, an outer radial extent and/or the radially outermost extent of the plurality of anti-migration supports 20 and/or the anti-migration loops in the radially expanded configuration and/or at the first angle $\theta_1$ may be substantially equal to the outer diameter of the first flared region 13 and/or the second flared region 15. In some embodiments, the outer radial extent and/or the radially outermost extent of the plurality of anti-migration supports 20 and/or the anti-migration loops in the radially expanded configuration and/or at the first angle $\theta_1$ may be within about +/−10%, about +/−5%, about +/−3%, about +/−1%, or another suitable range of the outer diameter of the first flared region 13 and/or the second flared region 15.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

The materials that can be used for the various components of the esophageal stent(s) and the various elements thereof disclosed herein may include those commonly associated with medical devices and/or stents. For simplicity purposes, the following discussion refers to the apparatus. However, this is not intended to limit the devices and methods described herein, as the discussion may be applied to other elements, members, components, or devices disclosed herein, such as, but not limited to, the esophageal stent, the expandable framework, the filaments, the anti-migration supports or loops, the covering, the outer sleeve and/or elements or components thereof.

In some embodiments, the apparatus, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the apparatus, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the apparatus in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the apparatus to achieve the same result.

In some embodiments, a degree of Magnetic Resonance Imaging (MM) compatibility is imparted into the apparatus and/or other elements disclosed herein. For example, the apparatus, and/or components or portions thereof, may be made of a material that does not substantially distort the image and create substantial artifacts (e.g., gaps in the image). Certain ferromagnetic materials, for example, may not be suitable because they may create artifacts in an MM image. The apparatus, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the apparatus and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An esophageal stent, comprising:
   an expandable framework including a body region formed of one or more interwoven filaments, the expandable framework having a first end, a second end, and a central longitudinal axis extending from the first end to the second end, the expandable framework being configured to expand from a radially collapsed configuration to a radially expanded configuration; and
   a polymeric outer sleeve disposed radially outward of and spaced apart from the body region of the expandable framework;
   wherein the expandable framework includes a plurality of anti-migration supports extending radially outward from the body region of the expandable framework toward the polymeric outer sleeve;
   wherein the plurality of anti-migration supports is a plurality of anti-migration loops each hingedly attached to the expandable framework at a base of the anti-migration loops.

2. The esophageal stent of claim 1, wherein the expandable framework is configured to self-expand from the radially collapsed configuration to the radially expanded configuration when unconstrained.

3. The esophageal stent of claim 1, wherein the plurality of anti-migration supports extends radially outward from the body region at an oblique angle to the central longitudinal axis.

4. The esophageal stent of claim 3, wherein the plurality of anti-migration supports is angled toward the second end of the expandable framework.

5. The esophageal stent of claim 3, wherein the oblique angle is greater than about 45 degrees and less than 90 degrees.

6. The esophageal stent of claim 1, wherein the expandable framework includes a first flared region proximate the first end and a second flared region proximate the second end;
   wherein the body region extends from the first flared region to the second flared region.

7. The esophageal stent of claim 1, wherein the expandable framework is encapsulated within a polymeric covering.

8. An esophageal stent, comprising:
   an expandable framework having a first end, a second end, and a central longitudinal axis extending from the first end to the second end, the expandable framework being configured to expand from a radially collapsed configuration to a radially expanded configuration; and
   a polymeric outer sleeve disposed radially outward of and spaced apart from a body region of the expandable framework;
   wherein the expandable framework includes a plurality of interwoven filaments;
   wherein at least a portion of the plurality of interwoven filaments extends radially outward beyond an outer diameter of the body region to form anti-migration loops;
   wherein the anti-migration loops extend from the body region at a first angle;
   wherein a base of each of the anti-migration loops forms a hinge portion such that the anti-migration loops are elastically deflectable from the first angle to a second angle less than the first angle;
   wherein the anti-migration loops extend radially outward from the body region to the polymeric outer sleeve.

9. The esophageal stent of claim 8, wherein the anti-migration loops are configured to deflect radially inward at the base when subjected to a radially inward force.

10. The esophageal stent of claim 9, wherein the expandable framework is configured to maintain a constant inner diameter when the anti-migration loops are subjected to the radially inward force.

11. The esophageal stent of claim 8, wherein an axial force applied to the expandable framework in a direction toward the second end in situ is transmitted radially outward through the anti-migration loops.

12. The esophageal stent of claim 8, wherein the expandable framework includes a first flared region proximate the first end and a second flared region proximate the second end;
   wherein the body region extends from the first flared region to the second flared region;
   wherein the first flared region and the second flared region have an outer diameter in the radially expanded configuration, and the outer diameter of the body region is less than the outer diameter of the first flared region and the second flared region;
   wherein an outer radial extent of the plurality of anti-migration loops in the radially expanded configuration is substantially equal to the outer diameter of the first flared region and the second flared region.

13. The esophageal stent of claim 8, wherein the first angle is an oblique angle.

14. An esophageal stent, comprising:
   a metallic expandable framework having a first end, a second end, and a central longitudinal axis extending from the first end to the second end, the expandable framework being configured to self-expand from a radially collapsed configuration to a radially expanded configuration when unconstrained; and
   a polymeric outer sleeve disposed radially outward of the expandable framework;
   wherein the expandable framework includes a first flared region proximate the first end, a second flared region proximate the second end, and a body region extending from the first flared region to the second flared region;
   wherein the expandable framework is encapsulated within a polymeric covering;
   wherein the expandable framework includes a plurality of anti-migration loops each hingedly attached to the expandable framework at a base of the plurality of anti-migration loops;
   wherein the plurality of anti-migration loops is heat set to be biased toward the expanded configuration.

15. The esophageal stent of claim 14, wherein the polymeric covering and the polymeric outer sleeve are fixedly attached together at the first flared region and the second flared region.

16. The esophageal stent of claim 14, wherein the plurality of anti-migration loops spaces the polymeric outer sleeve apart from the body region.

17. The esophageal stent of claim 14, wherein the body region maintains a fixed inner diameter when subjected to a radially inward force up to about 5 Newtons.

18. The esophageal stent of claim 17, wherein the plurality of anti-migration loops is configured to deflect radially inward toward the body region at the base when subjected to a radially inward force less than about 5 Newtons.

19. The esophageal stent of claim 14, wherein each of the plurality of anti-migration loops is formed of an arcuate segment of a filament of the expandable framework, wherein the arcuate segment of the filament forming the anti-migration loop is located between first and second segments of the filament helically extending around the expandable framework interwoven with other filaments of the expandable framework.

\* \* \* \* \*